(12) United States Patent
Weinstein

(10) Patent No.: US 12,016,752 B2
(45) Date of Patent: Jun. 25, 2024

(54) CORRECTIVE APPARATUS FOR DEFORMED EXTERNAL EAR

(71) Applicant: EarGear, LLC, Brooklyn, NY (US)

(72) Inventor: Gila R. Weinstein, Brooklyn, NY (US)

(73) Assignee: EarGear, LLC, Brooklyn, NY (US)

( * ) Notice: Subject to any disclaimer, the term of this patent is extended or adjusted under 35 U.S.C. 154(b) by 670 days.

(21) Appl. No.: 16/681,299

(22) Filed: Nov. 12, 2019

(65) Prior Publication Data

US 2020/0146891 A1    May 14, 2020

Related U.S. Application Data

(60) Provisional application No. 62/758,712, filed on Nov. 12, 2018.

(51) Int. Cl.
*A61F 11/20* (2022.01)
*A61F 5/058* (2006.01)
*A61F 11/00* (2022.01)

(52) U.S. Cl.
CPC .......... *A61F 11/20* (2022.01); *A61F 5/05891* (2013.01); *A61F 11/00* (2013.01); *A61F 2210/009* (2013.01); *A61F 2250/0082* (2013.01)

(58) Field of Classification Search
CPC .......... A61F 11/00; A61F 11/06; A61F 11/11; A61F 11/20; A61F 2210/009; A61F 2250/00; A61F 2250/0058; A61F 2250/0059; A61F 2250/0082; A61F 5/00; A61F 5/01; A61F 5/0102; A61F 5/04; A61F 5/05; A61F 5/058; A61F 5/05883; A61F 5/05891; A61F 2/50; A63B 71/085; A61H 39/04; H04R 25/65; H04L 67/00
See application file for complete search history.

(56) References Cited

U.S. PATENT DOCUMENTS

| | | | |
|---|---|---|---|
| 4,187,838 A | 2/1980 | Dubrowski | |
| 5,425,160 A | 6/1995 | Krapf | |
| 6,458,146 B1 * | 10/2002 | Kramer | A61H 39/04 606/189 |
| 6,517,557 B1 | 2/2003 | Sorribes | |
| 7,850,702 B2 | 12/2010 | Sorribes | |
| 8,136,530 B2 | 3/2012 | Byrd et al. | |

(Continued)

FOREIGN PATENT DOCUMENTS

| | | |
|---|---|---|
| AU | 2016238955 A1 | 11/2016 |
| CN | 206102794 U | 4/2017 |

(Continued)

OTHER PUBLICATIONS

Extended European Search Report for corresponding European Application No. 19885119.8 dated Jul. 13, 2022, 7 pages.

(Continued)

*Primary Examiner* — Ophelia A Hawthorne
*Assistant Examiner* — Gina McCarthy
(74) *Attorney, Agent, or Firm* — Farber LLC

(57) ABSTRACT

A non-surgical corrective apparatus for a deformed external ear is described. The corrective apparatus will be worn externally to correct a deformity or malformation on the external ear through molding over a period of time. Using a typical infant's ear as a guide, the corrective apparatus is configured to mold and reshape the deformed ear and correct its present deformities.

13 Claims, 13 Drawing Sheets

(56) References Cited

U.S. PATENT DOCUMENTS

| | | | |
|---|---|---|---|
| 8,167,942 B2 | 5/2012 | Byrd et al. | |
| 8,715,347 B2 * | 5/2014 | Servell | H04L 67/00 |
| | | | 606/204.15 |
| 8,852,277 B2 | 10/2014 | Byrd et al. | |
| 9,023,105 B2 | 5/2015 | Byrd et al. | |
| 10,362,411 B2 * | 7/2019 | Riemer | H04R 25/65 |
| 11,185,446 B2 * | 11/2021 | Bartlett | A61F 5/01 |
| 2009/0030358 A1 | 1/2009 | Byrd et al. | |
| 2009/0165805 A1 * | 7/2009 | Syrop | A63B 71/085 |
| | | | 128/861 |
| 2012/0124179 A1 | 5/2012 | Cappio et al. | |
| 2012/0124719 A1 | 5/2012 | Michlitsch et al. | |
| 2012/0179078 A1 | 7/2012 | Koehler | |
| 2013/0068238 A1 | 3/2013 | Parris et al. | |
| 2015/0051639 A1 | 2/2015 | Case et al. | |
| 2021/0282974 A1 * | 9/2021 | Zopf | A61F 5/05891 |

FOREIGN PATENT DOCUMENTS

| | | | | |
|---|---|---|---|---|
| ES | 2335178 A1 | 3/2010 | | |
| GB | 2304579 A * | 3/1997 | | A61F 11/004 |
| GB | 2304579 A | 3/1997 | | |
| WO | 2014/107532 A1 | 7/2014 | | |
| WO | 2014/167381 A1 | 10/2014 | | |
| WO | 2014167381 A1 | 10/2014 | | |
| WO | 2018053219 A1 | 3/2018 | | |

OTHER PUBLICATIONS

International Search Report & Written Opinion for PCT/US2019/060952 dated Jan. 29, 2020.

* cited by examiner

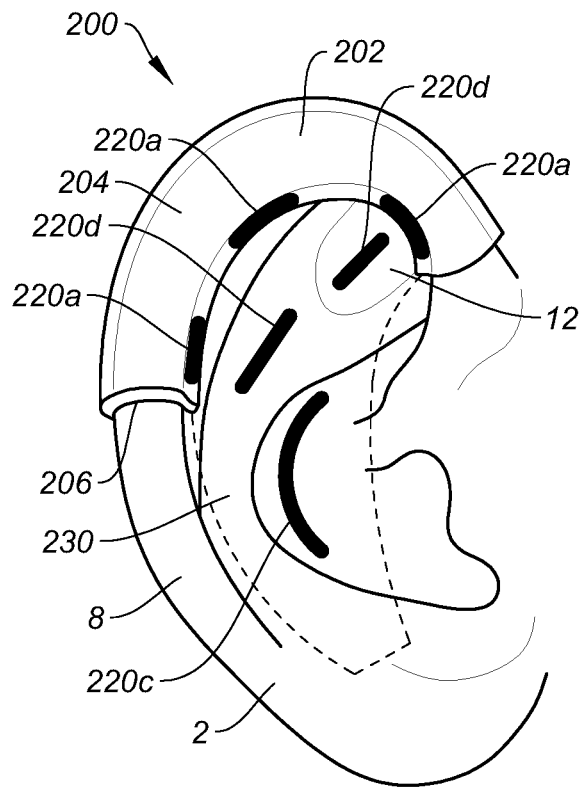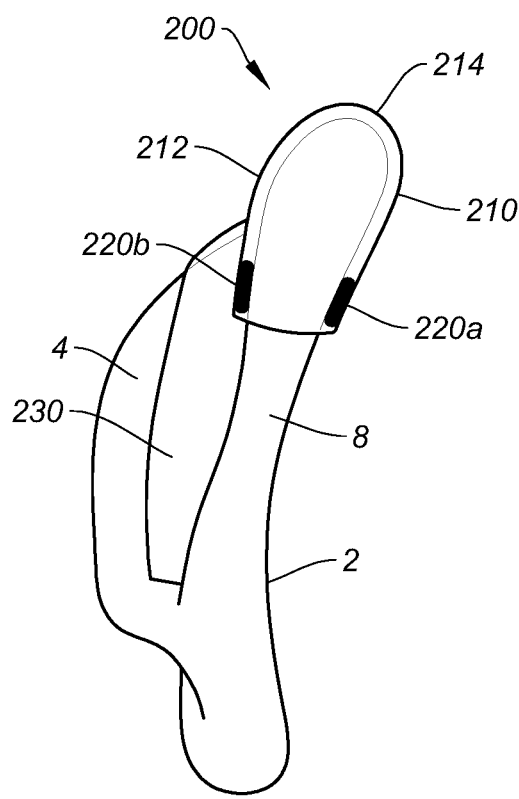
FIG. 3A  FIG. 3B
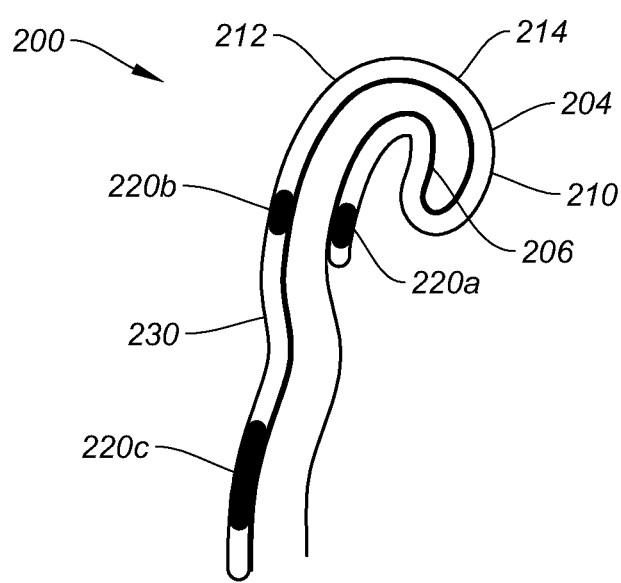
FIG. 3C

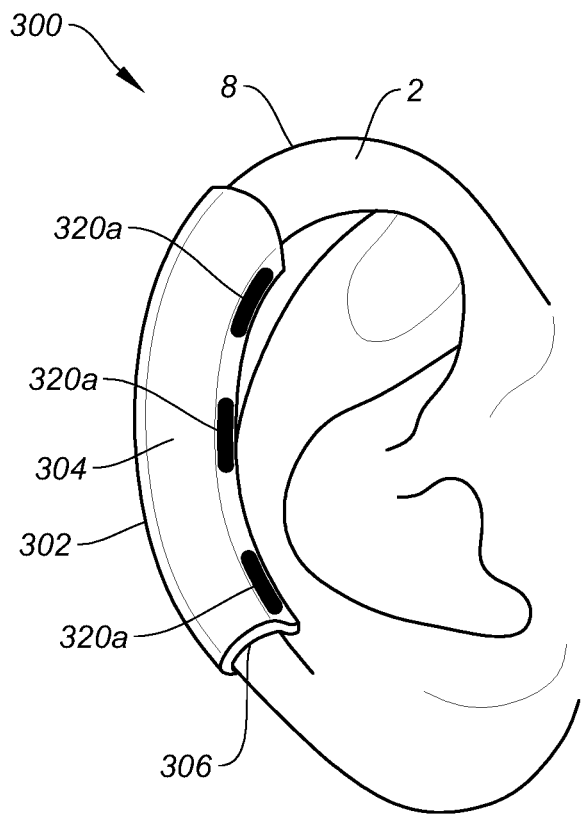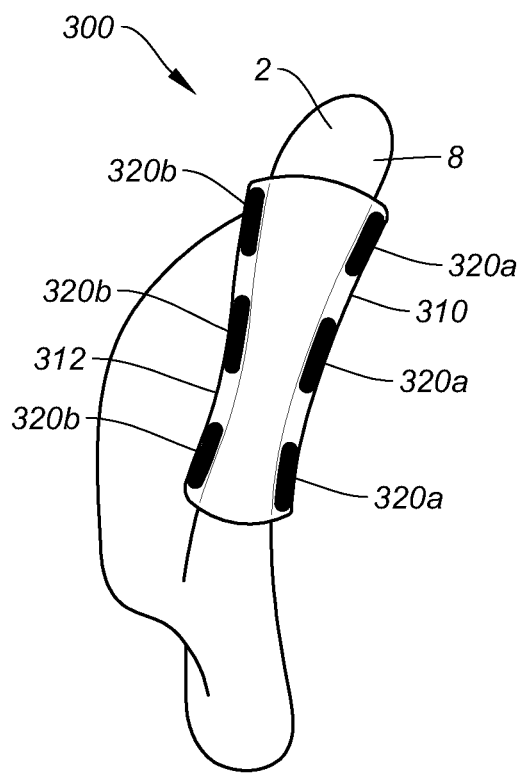
FIG. 4A  FIG. 4B
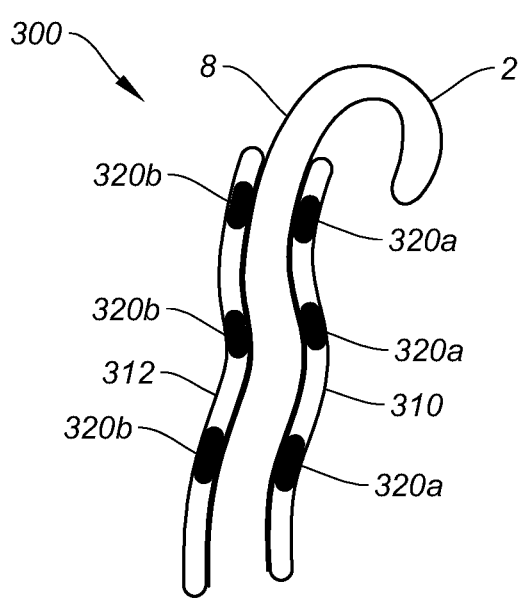
FIG. 4C

CORRECTIVE APPARATUS FOR DEFORMED EXTERNAL EAR

CROSS-REFERENCE TO RELATED APPLICATIONS

This application claims benefit of U.S. Provisional No. 62/758,712 filed Nov. 12, 2018 and entitled "Corrective Apparatus for Deformed External Ear," the contents of which are incorporated in their entirety by reference.

FIELD

The present disclosure relates to a non-surgical corrective apparatus for a deformed external ear. The corrective apparatus will be worn externally to correct a deformity or malformation on the external ear through molding over a period of time. Using a typical infant's ear as a guide, the corrective apparatus is configured to mold and reshape the deformed ear and correct its present deformities.

BACKGROUND

The external ear is an important biological structure that aids in human hearing. In newborns, the external ear can be deformed. An external ear deformity can cause a range of issues from cosmetic to hearing and developmental problems. Some deformities may require therapy or surgery to correct. A small percentage of deformities self-correct within the first week or two of life.

External ear shaping mechanisms are known. Examples of some of these external ear shaping mechanisms are provided below.

For instance, U.S. Pat. No. 7,850,702 pertains to a clamp in the form of a mainly U-shaped or V-shaped device that serves to non-invasively affect a cartilage fold on, for example the exterior ear, by exerting a stretching and compressive force.

U.S. Pat. No. 9,023,105 pertains to a system and method for correcting misshaped ears using a molding device having one or more braces supporting a scaphal mold.

U.S. Patent Application Publication No. 2012/0124719 pertains to methods and apparatuses for protecting the external ear from the elements, such as heat, cold, wind, rain and/or snow.

U.S. Patent Application Publication No. 2013/0068238 pertains to an ear protector and an ear protector wrap. In some embodiments, the ear protector comprises: an inner wall, an outer wall, and a curved joining wall.

International Patent Application Publication No. WO 2014/167381 pertains to a definitive preformed expander implant for ear reconstruction, using a reconstruction method which involves expanding autologous (the patient's own) tissues, and ideally performed in one surgical operation.

As noted, various systems and methodologies for correcting external ear deformities are known in the art. However, their structure and means of operation are substantially different from the present disclosure. The other inventions fail to solve all the problems taught by the present disclosure. Embodiments of the invention are presented in the drawings below and will be described in more detail herein.

SUMMARY

The present disclosure provides a non-surgical corrective apparatus for a deformed external ear. The corrective apparatus will be worn externally to correct a deformity or malformation on the external ear through molding over a period of time. Using a typical infant's ear as a guide, the corrective apparatus is configured to mold and reshape the deformed ear and correct its present deformities. The corrective apparatus may be used in combination with an additional external ear component, and/or as part of a corrective system to treat the ear.

In one exemplary embodiment of the present disclosure, a corrective apparatus for treating a deformity of an external ear is provided. The corrective apparatus may include a main body configured to enclose the deformity. The main body may have an outer surface and an inner surface defining sidewalls for forming a reshaping track for the external ear, the main body further being conformable to a desired shape and being able to maintain the desired shape during a time period of use sufficient to correct the deformity. The corrective apparatus may further include one or more attachment elements for securing the main body against the external ear.

The outer surface of the main body may have a generally convex shape, while the inner surface of the main body may have a generally concave shape. The main body may be configured to wrap around a helical rim of the external ear. For example, the main body may be configured to fold around the helical rim to form a front facing side extending anteriorly and rear facing side extending posteriorly.

According to an aspect of the disclosure, the one or more attachment elements may include magnets. The magnets may be positioned in opposing magnetic orientation within the front facing side and rear facing side of the main body to cause a magnetic attraction between the front facing side and rear facing side.

In one embodiment, the main body may further include an elongated rear platform for placement behind the external ear. This elongated rear platform may also include at least one magnet.

In another embodiment, an ear component for placement against the main body to create or reshape an antihelix and having at least one magnet is also provided.

In still another embodiment, an ear component for insertion into the concha bowl of the ear and having at least one magnet is also provided.

The main body may comprise a silicone, polymer, plastic or a blend thereof in some cases. In other cases, the main body may comprise a metal or metal alloy.

The main body may also include a metal wire. The metal wire may be embedded within the main body. In some embodiments, the metal wire is part of a metal mesh.

The corrective apparatus may be configured for use with an external ear of a newborn or young infant.

In another embodiment, a corrective system for treating a deformity of an external ear is provided. The corrective system may include a first corrective component having a main body configured to enclose the deformity. The main body may have an outer surface and an inner surface defining sidewalls for forming a reshaping track for the external ear. The main body may further be conformable to a desired shape and being able to maintain the desired shape during a time period of use sufficient to correct the deformity. In addition, the main body may have an inner flange and one or more magnets within the inner flange.

The corrective system may also include a second corrective component having a main body and a stem extending from the main body, the stem being configured for insertion into the concha bowl of the ear. The main body may have one or more magnets to create a magnetic attraction with the one or more magnets of the first corrective component. The stem of the second corrective component may further include a protrusion and be configured for insertion into the concha bowl.

In one embodiment, the one or more magnets of the first corrective component are embedded within the inner flange. In another embodiment, the one or more magnets of the first corrective component are contained within one or more pockets within the inner flange.

Similar to the previous embodiment, the outer surface of the main body may have a generally convex shape, while the inner surface of the main body may have a generally concave shape. The main body may be configured to wrap around a helical rim of the external ear. For example, the main body may be configured to fold around the helical rim to form a front facing side extending anteriorly and rear facing side extending posteriorly. One or more magnets may be provided and positioned on the rear facing side. These one or more magnets on the rear facing side may be opposite in polarity to the one or more magnets of the inner flange, in order to create a magnetic connection between the front facing side and rear facing side through the ear.

The main body may comprise a silicone, polymer, plastic or a blend thereof in some cases. In other cases, the main body may comprise a metal or metal alloy.

The main body may also include a metal wire. The metal wire may be embedded within the main body. In some embodiments, the metal wire is part of a metal mesh.

The corrective apparatus may be configured for use with an external ear of a newborn or young infant.

In yet another embodiment, a corrective apparatus for treating a deformity of an external ear is provided. The corrective apparatus may include a main body configured to enclose the deformity, the main body having a first corrective flap and a second corrective flap, the main body being configured to be folded over a rim of the external ear, the main body further being conformable to a desired shape and being able to maintain the desired shape during a time period of use sufficient to correct the deformity, and one or more attachment elements for securing the main body against the external ear.

In one embodiment, the one or more attachment elements comprise magnets. The one or more magnets may be positioned on the first corrective flap and second corrective flap to create a magnetic attraction between the first corrective flap and second corrective flap during use. In some embodiments, the main body may have a generally elongate shape.

In still another embodiment, a kit for treating a deformity of an external ear is provided. This kit may include a corrective apparatus and corrective system as previously described. In addition, the kit may include a guide for determining which of the corrective apparatuses or corrective system to select for treating the deformity. This guide may comprise a transparency having an outline of a model human ear thereon. The outline of the model human ear may contain sections corresponding to at least one of the corrective apparatuses or corrective system. The sections may be designated by lines, and/or also may be color coded.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 1A and 1B illustrate various views of an exemplary human ear, in which:

FIG. 1A shows a front view of a right ear; and

FIG. 1B shows the ear of FIG. 1A from a side view.

FIGS. 2A to 2C illustrate various views of an exemplary embodiment of a corrective apparatus of the present disclosure, in which:

FIG. 2A shows a front view of the corrective apparatus in use with a right human ear;

FIG. 2B shows a side view of the corrective apparatus and right human ear of FIG. 2A; and FIG. 2C shows a cross-sectional view of the corrective apparatus and right human ear of FIG. 2A.

FIGS. 3A to 3C illustrate various views of another exemplary embodiment of a corrective apparatus of the present disclosure, in which:

FIG. 3A shows a front view of the corrective apparatus in use with a right human ear;

FIG. 3B shows a side view of the corrective apparatus and right human ear of FIG. 3A; and FIG. 3C shows a cross-sectional view of the corrective apparatus and right human ear of FIG. 3A.

FIGS. 4A to 4C illustrate various views of still another exemplary embodiment of a corrective apparatus of the present disclosure, in which:

FIG. 4A shows a front view of the corrective apparatus in use with a right human ear;

FIG. 4B shows a side view of the corrective apparatus and right human ear of FIG. 4A; and FIG. 4C shows a cross-sectional view of the corrective apparatus and right human ear of FIG. 4A.

FIGS. 8A to 10B illustrate various views of an exemplary embodiment of a corrective system of the present disclosure, in which:

FIG. 8A shows a front perspective view of the corrective system in use with a left human ear;

FIG. 10B shows a rear perspective view of the second corrective component of the corrective system of FIG. 10A.

FIGS. 11A to 12B illustrate various views of another exemplary embodiment of a first corrective component for use in a corrective system, in which:

FIG. 11A shows a front perspective view of the first corrective component in use with a left human ear;

FIG. 12B shows another rear perspective view of the first corrective component of FIG. 12A.

FIGS. 13A to 14B illustrate various views of yet another exemplary embodiment of a first corrective component for use in a corrective system, in which:

FIG. 13A shows a front perspective view of the first corrective component in use with a left human ear;

FIG. 14B shows another rear perspective view of the first corrective component of FIG. 14A.

DETAILED DESCRIPTION OF THE EMBODIMENTS

The present disclosure provides a non-surgical corrective apparatus for a deformed external ear. The corrective apparatus will be worn externally to correct a deformity or malformation on the external ear through molding over a period of time. Using a typical infant's ear as a guide, the corrective apparatus is configured to mold and reshape the deformed ear and correct its present deformities. The corrective apparatus may be used in combination with an additional external ear component, and/or as part of a corrective system to treat the ear.

Figure 1A:
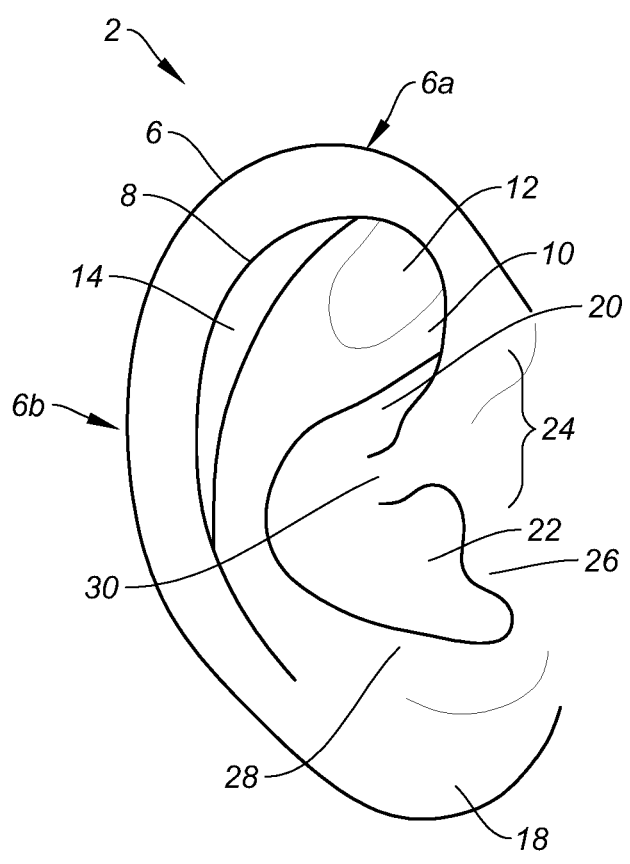
Figure 1B:
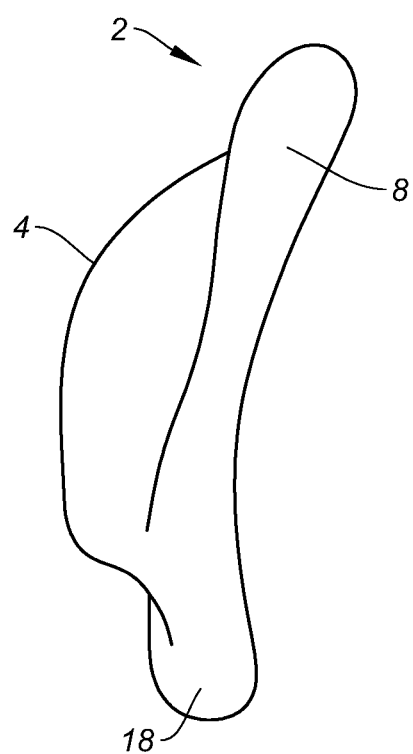

FIGS. 1A and 1B illustrate a normal human ear. The figures may be referred to for anatomical context and perspective to appreciate and understand the corrective apparatus of the present disclosure. In general, the visible part of the external ear is called the auricle. The auricle is also referred to as the pinna. The auricle is composed of a thin plate of cartilage. The cartilage is covered with skin. The cartilage is also connected to the surrounding parts by ligaments and muscles. Furthermore, the cartilage is connected to the commencement of the ear canal by fibrous tissue.

FIG. 1A shows a front view of a right ear 2 and FIG. 1B shows the ear 2 from a side view. The human ear 2 extends from the base of the ear 4 that attaches to the scalp skin. The major outer curved portion of the ear 2 is generally referred to as the helix 6. The helix 6 extends from the superior helix 6a to the descending helix 6b, as indicated in FIG. 1A. The ear 2 also includes the helical rim 8 and the antihelix 10 within the interior of the external ear 2 itself, as shown in FIG. 1A. The scapha 14 is the space between the helical rim 8 and the antihelix 10. The triangular fossa 12 is located at the upper inner portion. The ear 2 also includes the cymba 20 and cavum 22, which collectively can be generally referred to as the concha, or concha bowl 24. Outside the concha bowl 24 is the tragus 26 and antitragus 28, while the crus 30 is located between the cymba 20 and the cavum 22 of the concha bowl 24. The bottom of the ear 2 extends into a lobule, or lobe 18, as shown in FIGS. 1A and 1B.

As mentioned, infants are sometimes born with external ear deformities or malformations, and external ear shaping mechanisms are known to exist. However, these existing ear shaping mechanisms do not always adequately address the unique concerns of newborns or young infants. For example, an ideal external ear remodeling mechanism would take into account the delicate skin of newborns and young infants, and avoid causing any harm or further deformities to that area of the patient with use of the ear remodeling mechanism. Also, since the newborn and young infant ear is much smaller in scale than for a normal human adult, the ear shaping mechanism also needs to be appropriately sized as well as scaled (i.e., not too bulky or heavy) to be an effective treatment for a newborn and young infant.

The present disclosure provides various embodiments of corrective apparatuses configured to conform a shape of the deformed external ear of a newborn or infant to a shape of a model external ear when worn over a time period. In some embodiments, the corrective apparatus may be used in combination with an additional external ear component, and as part of a corrective system to treat the external ear deformity. In use, the corrective apparatuses or corrective systems act as a remodeling guide, enveloping and applying compression or exerting pressure on the ear deformity while also providing a physical support within its inner walls. The inner walls or sidewalls create a track to guide the remodeling process and to urge the remodeled ear to a desired ear shape. It is to be understood that what is meant by the term "remodeling" throughout this disclosure is the correction of the shape of the ear deformity.

These corrective apparatuses and corrective systems may be made from a medical grade silicone, polymer, plastic, polymeric blend, or similar soft and pliable material suitable for human use. In some embodiments, the material may be transparent, translucent, or semi-opaque, and allow the physician to see the patient's ear through the apparatus or system during use to monitor progress. The corrective apparatuses may also be formed of a metal material as well. The metal material may be coated or embedded within a polymeric or plastic coating or layer to further ensure that a smooth and non-damaging surface is provided for the patient.

To further ensure that the corrective apparatus and corrective systems stay securely in place on the patient's ear, attachment mechanisms may be employed. In one embodiment, the attachment mechanism may comprise magnets that create a strong but safe magnetic connection through the patient's ear and allow the corrective apparatus or corrective system to remain in proper position during the period of use.

The magnets may take on any suitable shape and/or size effective to maintain the corrective apparatus or corrective system in position relative to the patient's ear. It is understood that the magnets may be round, oval, square, rectangular, elongate, or any other shape. Of course, while magnets are described and shown, it is understood that other attachment mechanisms may also be employed, such as for example, medical grade adhesives or temporary glues, surgical tapes, Velcro or hook and loop materials, and other such known skin attachment mechanisms. For example, it is also possible to utilize a dovetail, or male-female grooved connection. It is further understood that a combination of attachment mechanisms may also be used together, such that magnets along with surgical tape may be used together, if so desired. The attachment mechanisms should ideally be strong enough to maintain the corrective apparatus or corrective system in place during the time period of use, but allow easy removability as well as leave no residue or cause further damage to the patient's skin upon removal.

Figure 2A:
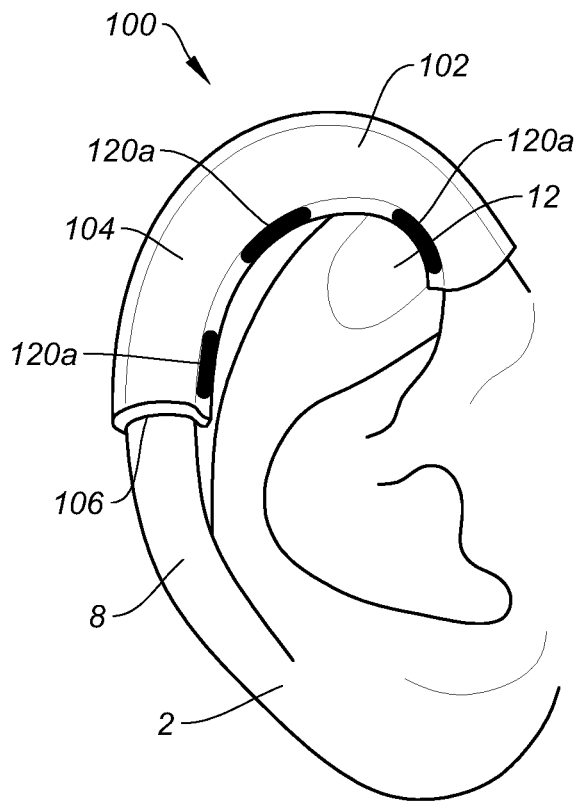
Figure 2B:
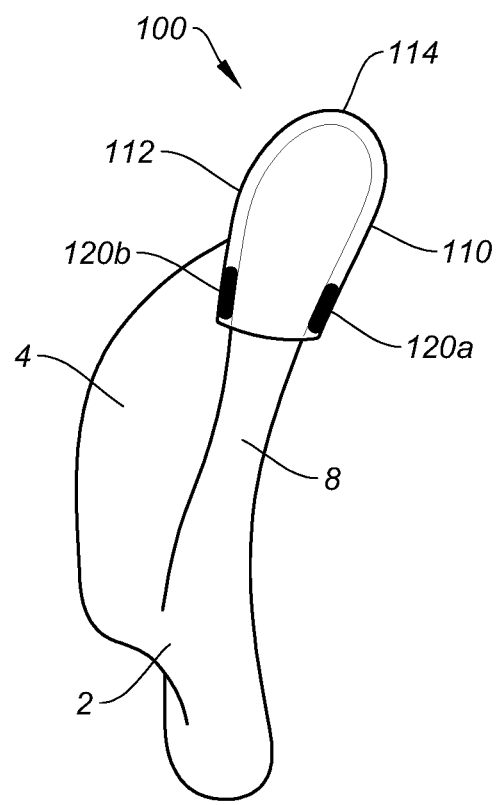
Figure 2C:
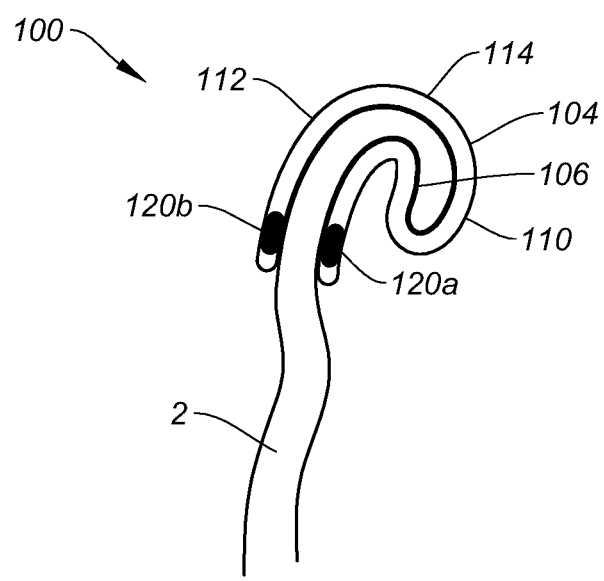

Turning now to the drawings, FIGS. 2A to 2C illustrate various views of an exemplary embodiment of a corrective apparatus 100 of the present disclosure for remodeling a deformed external ear into a model, or normal, external ear. FIG. 2A shows a front view of the corrective apparatus 100 in use with a right human ear 2, while FIG. 2B shows a side view of the corrective apparatus 100 in use FIG. 2C shows a cross-sectional view of the corrective apparatus 100 in use.

The corrective apparatus 100 may include a main body 102 for placement around the helical rim 8 of the ear 2. As shown in FIGS. 2A and 2C, the main body 102 can include a generally convex outer surface 104 and a generally concave inner surface 106 when in use. Further, when in use, the main body 102 has a front facing side 110 that extends anteriorly, and a rear facing side 112 that extends posteriorly. The main body 102 can also include a curved topside 114, as shown in FIGS. 2B and 2C. As shown in cross-section, the main body 102 can have a generally C-shape with elongated tails or terminal ends.

In use, the corrective apparatus 100 may be placed on the deformed helical rim 8 of the newborn or young infant for a time period sufficient to allow the deformed ear to remodel itself. The main body 102 may be provided with a preformed shape corresponding to a desired shape of a normal human ear.

Alternatively, the main body 102 may be molded or shaped during implementation. In such a case, the main body 102 is flexible and conformable, but also sufficiently resilient, or stiff, and be able to maintain this shape in order to provide the necessary structural support and physical pressure on the patient's ear to allow the ear to remodel itself. For example, the main body 102 may be bendable and moldable, and able to maintain its shape after molding, such that the physician can sculpt the main body 102 of the corrective apparatus 100 into the desired ear shape on the patient's ear. In one embodiment, this sculpting may be accomplished by providing the main body 102 with a flexible wire (as shown in FIGS. 8A and 8B, 9A and 9B, 11A, 12A, 13A and 14A) or wire mesh (as shown in FIGS. 15A and 15B). In some cases, this would also allow the main body 102 to be provided as a more planar, or flatter component prior to use, and then shaped to the configuration shown in FIGS. 2A to 2C. This design would also allow for incremental shaping, since the physician would have the ability to shape the main body 102 incrementally over a time period to incrementally match the patient's ear to the shape of the model external ear. This feature would be especially helpful in cases of severe deformity or where the deformities may exist in distinct separate locations on the patient's ear.

In another embodiment, the main body 102 may be formed of a resilient polymer or metal that would allow the main body 102 to be shaped by the physician. Thus, the main body 102 may be formed from a material suitable to allow sculpting as described above.

To further ensure that the corrective apparatus 100 stays securely in place on the patient's ear 2, attachment mechanisms may be employed. In one embodiment, the attachment mechanism may comprise magnets 120a, 120b. At least one pair of magnets having opposite polarity (i.e., +/− poles) may be used to form a magnetic connection through the patient's ear 2 to keep the main body 102 securely on the ear 2. Of course, more than one pair of magnets 120a, 120b may be utilized, depending on the size of the main body 102, such as shown in FIGS. 2B and 2C. These magnets 120a, 120b may be contained within the main body 102 itself, as shown. The magnets 120a, 120b are positioned such that they form a magnetic connection through the patient's ear 2 to ensure that the corrective apparatus 100 remains in place over the desired time period necessary to allow the ear 2 to reshape itself.

As mentioned, the magnets may take on any suitable shape and/or size effective to maintain the main body 102 in position relative to the patient's ear 2. While the magnets 120a, 120b are shown as being elongate bars, it is understood that the magnets may be round, oval, square, rectangular, or any other shape. Of course, while magnets are described and shown, it understood that other attachment mechanisms may also be employed, such as for example, adhesives or temporary glues, tapes and other such skin attachment mechanisms.

FIGS. 3A to 3C illustrate various views of another exemplary embodiment of a corrective apparatus 200 of the present disclosure. In particular, FIG. 3A shows a front view of the corrective apparatus 200 in use while FIG. 3B shows a side view of the corrective apparatus 200 in use. A cross-sectional view of the corrective apparatus 200 in use is provided in FIG. 3C.

Corrective apparatus 200 shares similar features to corrective apparatus 100 described above. Like corrective apparatus 100, the corrective apparatus 200 may include a main body 202 for placement around the helical rim 8 of the ear 2. As shown in FIGS. 3A and 3C, the main body 202 can include a generally convex outer surface 204 and a generally concave inner surface 206 when in use. Further, when in use, the main body 202 has a front facing side 210 that extends anteriorly, and a rear facing side 212 that extends posteriorly. The main body 202 can also include a curved topside 214, as shown in FIGS. 2B and 2C. As shown in cross-section, the main body 202 can have a generally C-shape with elongated terminal ends extending from the C portion of the main body 202.

In addition, corrective apparatus 200 can include an elongated rear platform 230 that extends posteriorly from the main body 202. The elongated rear platform 230 may be shaped and sized to nest behind the ear 2 and against the base of the ear 4, as shown in FIGS. 3B and 3C. This elongated rear platform 230 may be useful to provide additional structural force against the patient's ear 2 and, along with an opposing force on the opposite side of the ear 2, holds the ear 2 closer to the scalp skin. This is useful when the desired result is to remodel the patient's ear 2 to lie closer to the patient's head. That is, the elongated rear platform 230 may be helpful to keep the patient's ear 2 from extending too far out. Accordingly, this additional support element assists with the positioning of the patient's ear 2 while the other portions of the corrective apparatus 200 addresses the shape of the patient's ear 2.

Similar to corrective apparatus 100, attachment mechanisms may be employed. In one embodiment, the attachment mechanism may comprise one or more pair of complementary magnets 220a, 220b. As shown in FIGS. 3B and 3C, one or more pairs of magnets having opposite polarity (i.e., +/− poles) may be used to form a magnetic connection through the patient's ear 2 to keep the main body 202 securely on the ear 2. These magnets 220a, 220b may be contained within the main body 202 itself, as shown. The magnets 220a, 220b are positioned such that they form a magnetic connection through the patient's ear 2 to ensure that the corrective apparatus 200 remains in place over the desired time period necessary to allow the ear 2 to remodel itself.

In addition, additional magnets 220c, 220d may also be employed with corrective apparatus 200. These additional magnets 220c, 220d may be positioned on the elongated rear platform 230 and cooperate with magnets of a complementary polarity secured to the inner surface of the patient's external ear 2 using adhesive, tape, etc. The magnets 220a, 220*b*, 220*c*, 220*d* may take any shape or size suitable to ensure that the main body 202 stays in position relative to the patient's ear 2.

FIGS. 4A to 4C illustrate various views of still another exemplary embodiment of a corrective apparatus 300 of the present disclosure. FIG. 4A shows a front view of the corrective apparatus 300 in use, while FIG. 4B shows a side view of the corrective apparatus 300 in use. A cross-sectional view of the corrective apparatus 300 in use is shown in FIG. 4C.

Corrective apparatus 300 shares similar features to corrective apparatus 100 described above. Like corrective apparatus 100, the corrective apparatus 300 may include a main body 302 for placement around the helical rim 8 of the ear 2. As shown in FIGS. 4A and 4C, the main body 302 can include a generally convex outer surface 304 and a generally concave inner surface 306 when in use. Further, when in use, the main body 302 has a front facing side 310 that extends anteriorly, and a rear facing side 312 that extends posteriorly. As shown in cross-section, the main body 202 can have a generally C-shape and be used for treating the descending helix 6*b* of the ear. As such, the corrective apparatus 300 has a generally elongate overall shape and serve as a C-clamp around the helical rim 8 of the ear 2, as shown.

Similar to corrective apparatus 100, corrective apparatus 300 may be secured in place on the patient's ear 2 with attachment mechanisms. In one embodiment, the attachment mechanism may comprise magnets 320*a*, 320*b*. One or more pairs of magnets having opposite polarity (i.e., +/− poles) may be used to form a magnetic connection through the patient's ear 2 and keep the main body 302 securely on the ear 2. The number of pair of magnets 320*a*, 320*b* may vary, depending on the size of the main body 102. These magnets 320*a*, 320*b* may be contained within the main body 302 itself, as shown. The magnets 320*a*, 320*b* are positioned such that they form a magnetic connection through the patient's ear 2 to ensure that the corrective apparatus 300 remains in place over the desired time period necessary to allow the ear 2 to reshape itself.

Figure 5:
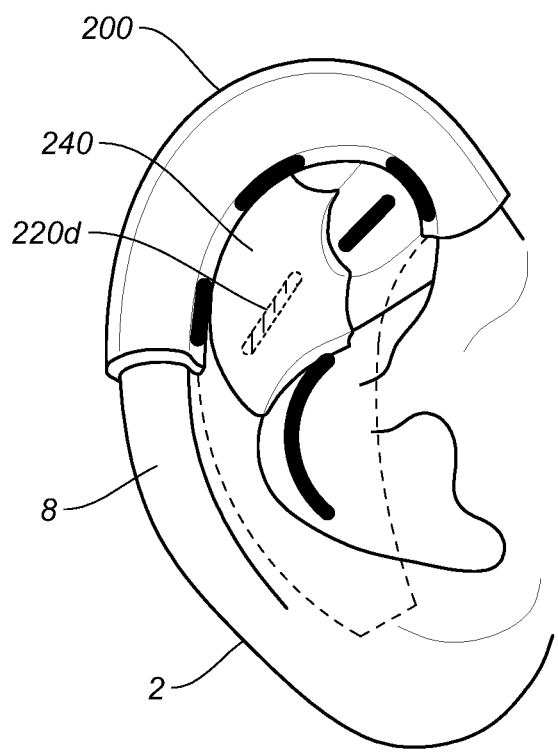
FIG. 5 illustrates the corrective apparatus of FIG. 3A in use with a right human ear and in combination with an additional external ear component.

The corrective apparatuses 100, 200, 300 of the present disclosure may be used alone or in combination with other ear components. For example, FIG. 5 illustrates corrective apparatus 200 in use with a right human ear and in combination with an additional external ear component 240. This additional external ear component 240 may be positioned over the antihelix 10, and aid in the creation of, or reshaping of, a desired antihelix 10, and further serve to assist in the remodeling of the patient's ear 2. In addition, the external ear component 240 may also serve to further support the corrective apparatus 200 during the time period of use.

Figure 6:
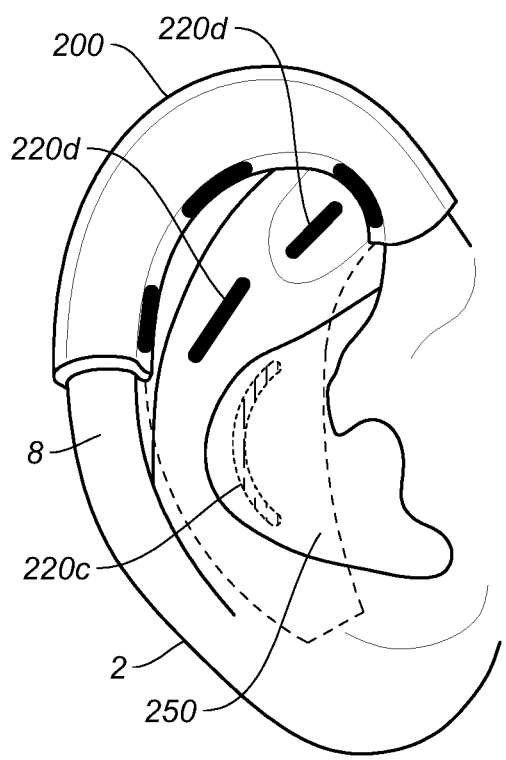
FIG. 6 illustrates the corrective apparatus of FIG. 3A in use with a right human ear and in combination with still another additional external ear component.

As shown in FIG. 5, the additional external ear component 240 is configured to have a shape and geometry that enables it to be fitted at the top portion of the patient's ear 2 and near the triangular fossa 12. In another embodiment, the additional external ear component 250 may be configured to have a shape and geometry to fit into the concha, or within the concha bowl 24 of the ear 2, as shown in FIG. 6.

Figure 7:
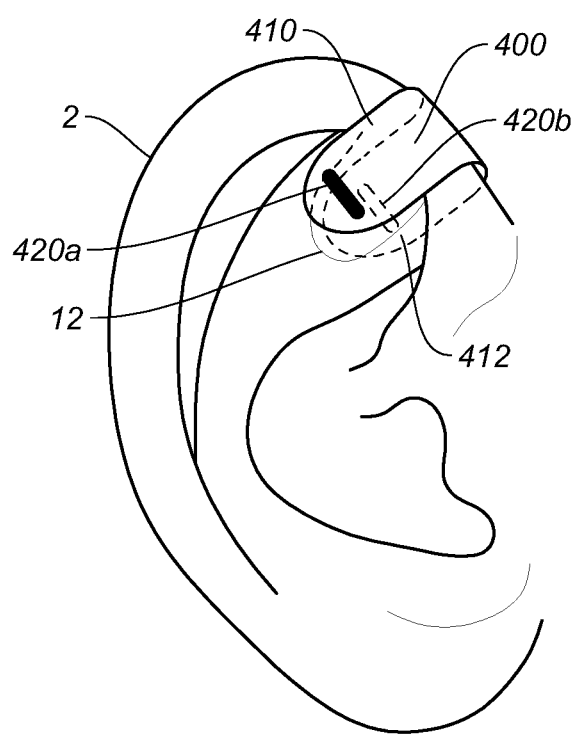
FIG. 7 illustrates a front view of yet another exemplary embodiment of a corrective apparatus of the present disclosure, in use with a right human ear.

FIG. 7 illustrates another exemplary embodiment of a corrective apparatus 400 of the present disclosure. Corrective apparatus 400 may be configured as an ear clip that is intended to be used to treat "hidden" ear deformities or cryptotia. The corrective apparatus 400 may be configured for use at the root of the helix of the ear 2. In some patients, this portion of the ear 2 may be hidden under the scalp skin, in a condition called cryptotia. The corrective apparatus 400 described herein and shown in FIG. 7 may be configured with a pair of flaps 410, 412 which allow the corrective apparatus 400 to clip over the ear 2, as shown, and keep the portion of the ear from refolding onto itself. Similar to the other corrective apparatuses previously described, attachment mechanisms such as magnets 420*a*, 420*b* may be utilized. As illustrated, at least a pair of magnets 420*a*, 420*b* of complementary polarity may be employed with the corrective apparatus 400 to create a magnetic connection through the patient's ear 2 and ensure that the corrective apparatus 400 stay in position during use.

Figure 8A:
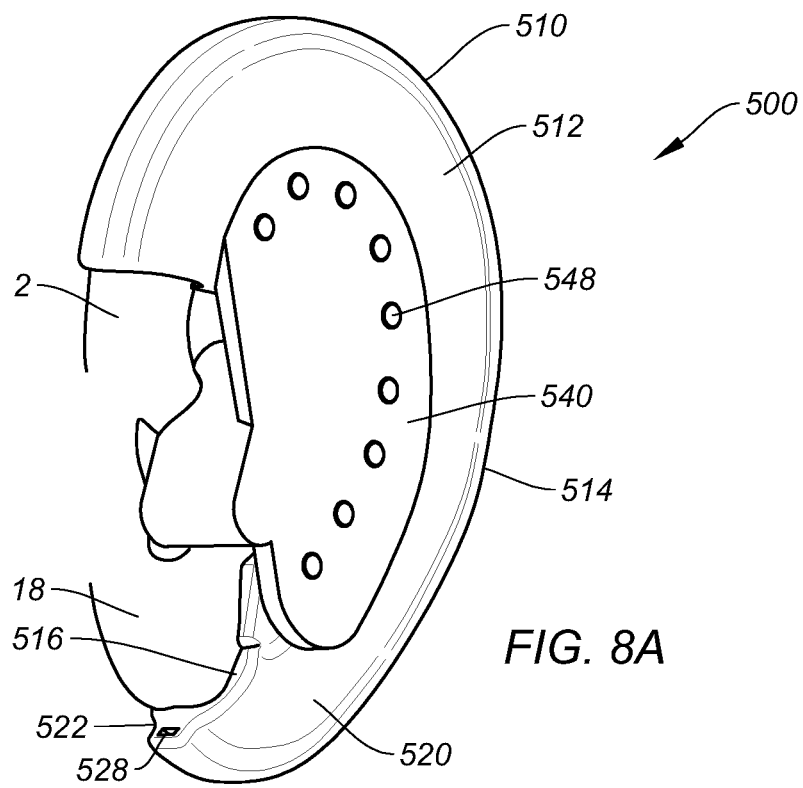
Figure 8B:
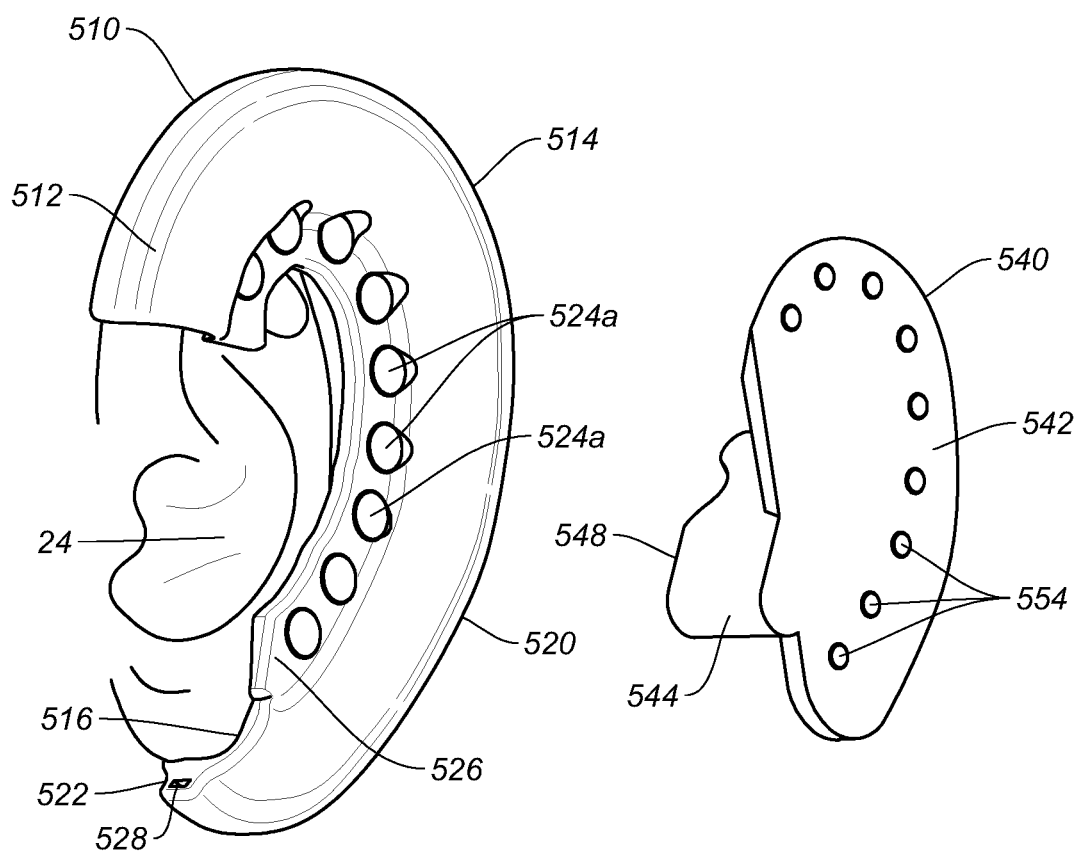
FIG. 8B shows an exploded view of the corrective system of FIG. 8A.
Figure 9A:
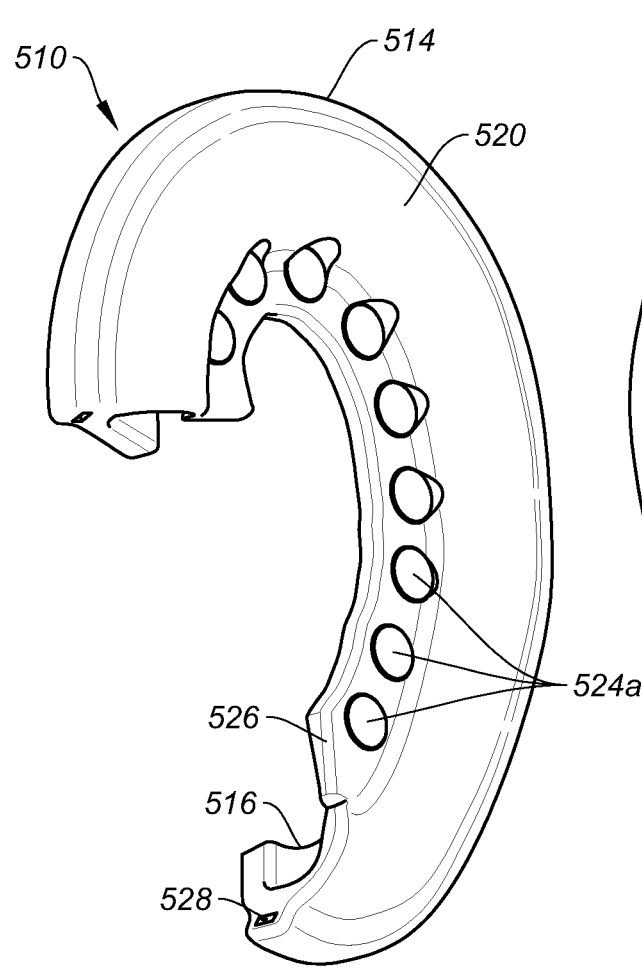
FIG. 9A shows a front perspective view of a first corrective component of the corrective system of FIG. 8A.
Figure 9B:
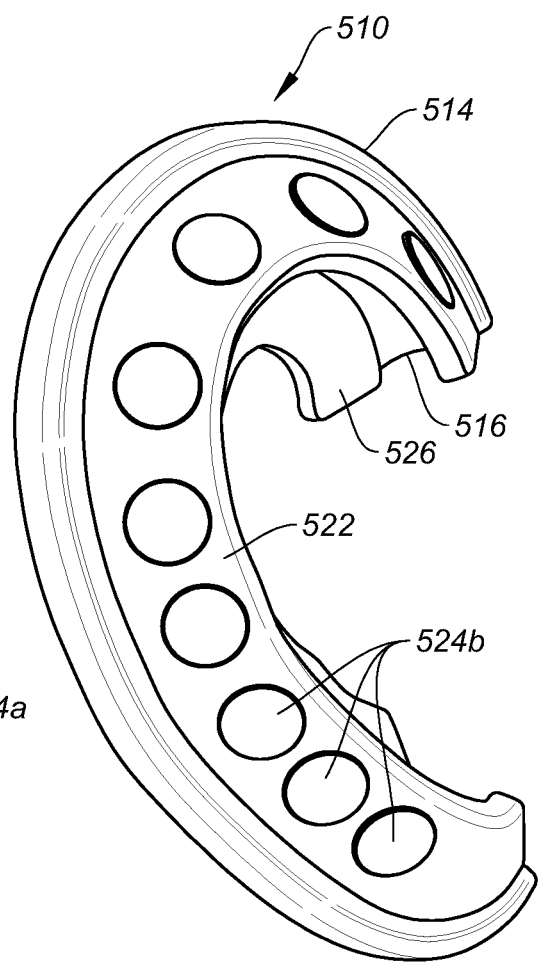
FIG. 9B shows a rear perspective view of the first corrective component of the corrective system of FIG. 9A.
Figure 10A:
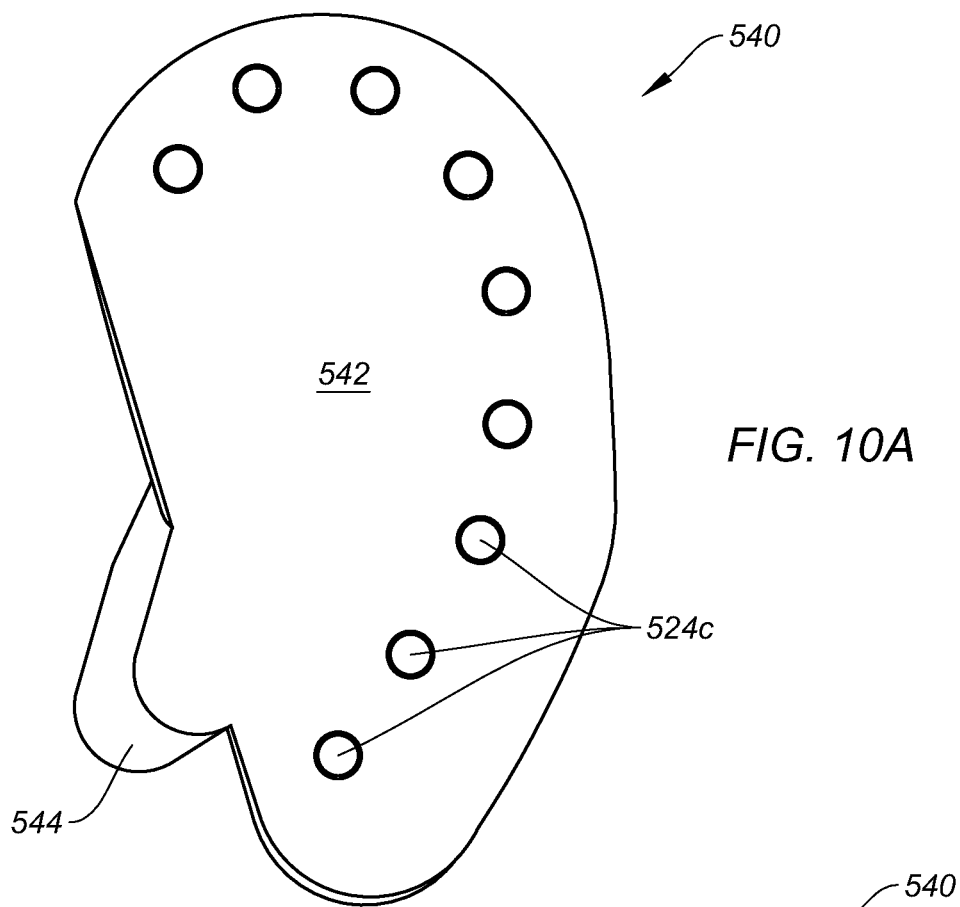
FIG. 10A shows a front perspective view of a second corrective component of the corrective system of FIG. 8A.
Figure 10B:
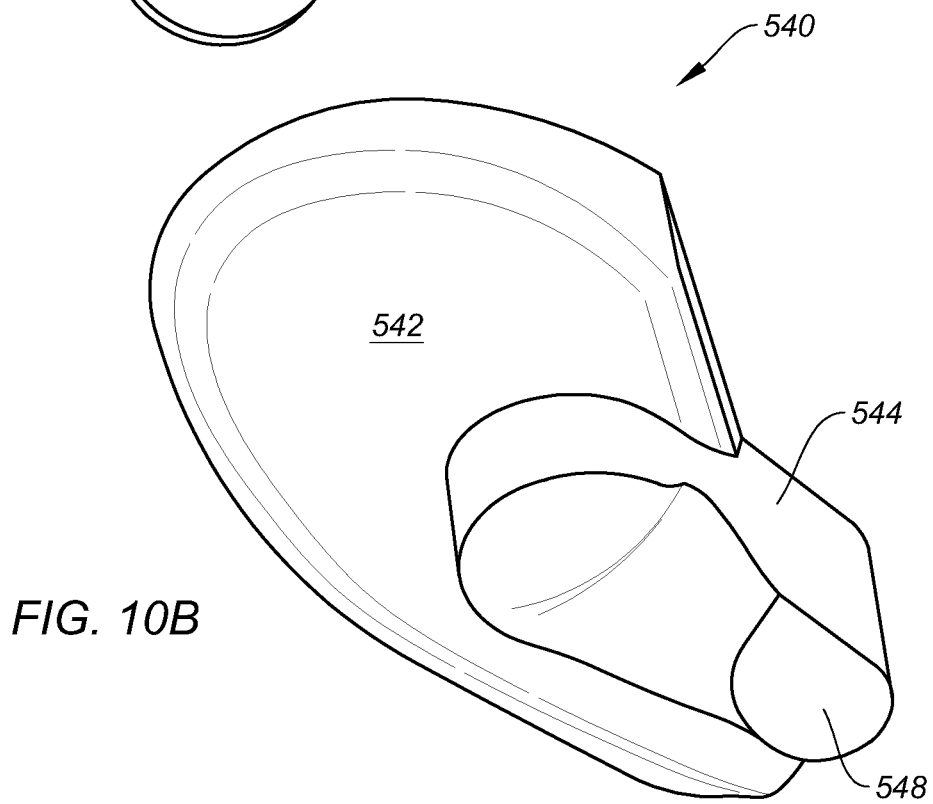

FIGS. 8A to 10B illustrate various views of an exemplary embodiment of a corrective system 500 of the present disclosure. FIG. 8A shows a front perspective view of the corrective system 500 in use with a left human ear 2, while FIG. 8B shows an exploded view of the corrective system 500. FIG. 9A shows a front perspective view of a first corrective component 510 of the corrective system 500, while FIG. 9B shows a rear perspective view of the first corrective component 510. FIG. 10A shows a front perspective view of a second corrective component 540 of the corrective system 500, while FIG. 10B shows a rear perspective view of the second corrective component 540.

As shown, corrective system 500 may comprise a first corrective component 510 that serves a similar purpose and is similarly configured like corrective apparatuses 100, 200, 300 previously described. Like corrective apparatuses 100, 200, 300, the main body 512 of the first corrective component 510 may be configured for placement around the helical rim 8 of the ear 2. As shown in FIGS. 9A and 9B, the main body 512 can include a generally convex outer surface 514 and a generally concave inner surface 516. Further, the main body 512 has a front facing side 520 that extends anteriorly, and a rear facing side 522 that extends posteriorly.

The main body 512 may include therein one or more metal wires or filaments 528, which may be embedded within the main body 512. The metal wires or filaments 528 may extend around the main body 512 along its spine, as illustrated in FIGS. 8A, 8B and 9A. However, it is understood that the metal wires or filaments 528 may be located anywhere along the length of the main body 512, such as for example, positioned around the entire surface or at a discrete portion of the main body. The metal wires 528 allow the main body 512 to be bent to a desired shape, while maintaining this shape after manipulation by the physician.

A flange 526 extends from the interior of the main body 512, as shown in FIGS. 8B, 9A and 9B. One or more magnets 524*a* may be positioned around the flange 526, as shown in detail in FIGS. 8B and 9A. The magnets 524*a* may be embedded within the flange 526, or held within pockets or cutouts formed in the flange 526. This flange 526 also serves to remodel the patient's ear with a desired scaphoid fossa, by assisting in the widening of narrowed space. Complementary magnets 524*b* having opposed polarity may be provided along the rear facing side 522 of the main body 512, as shown in FIG. 9B. As discussed above, during use, the magnets 524*a*, 524*b* create a strong magnetic connection through the patient's ear 2 and helps to maintain the first, outside component 510 in position.

Corrective system 500 may further comprise a second corrective component 540 that is configured to complement and fit against first corrective component 510. As shown in FIGS. 8A and 8B, the second corrective component 540 may be configured as a concha bowl insert, having a main body 542 and a stem 544 extending therefrom. The stem 544 may further include a protrusion 548. The stem 544 and protrusion 548 are configured to fit within the concha bowl 24 of the patient's ear 2. The second corrective component 540 further helps to mold and widen the concha bowl 24 during use.

One or more complementary magnets 524c may be provided on the main body 542 of the second corrective component 540, such as shown in FIG. 8B. The magnets 524c may be opposite in polarity with respect to magnets 524a of the first corrective component 510. When used together, the magnets 524a, 524c form a magnetic connection between the two components 510, 540 of the corrective system 500.

The second corrective component 540 has a geometry and shape that matches and complements the first corrective component 510. In use, the second corrective component 540 nests securely within the first corrective component 510. Together, the corrective system 500 can be anchored onto the patient's ear through the stem 544 of the second corrective component 540 which is configured to fit within the concha bowl 24 of the patient's ear 2.

Figure 11A:
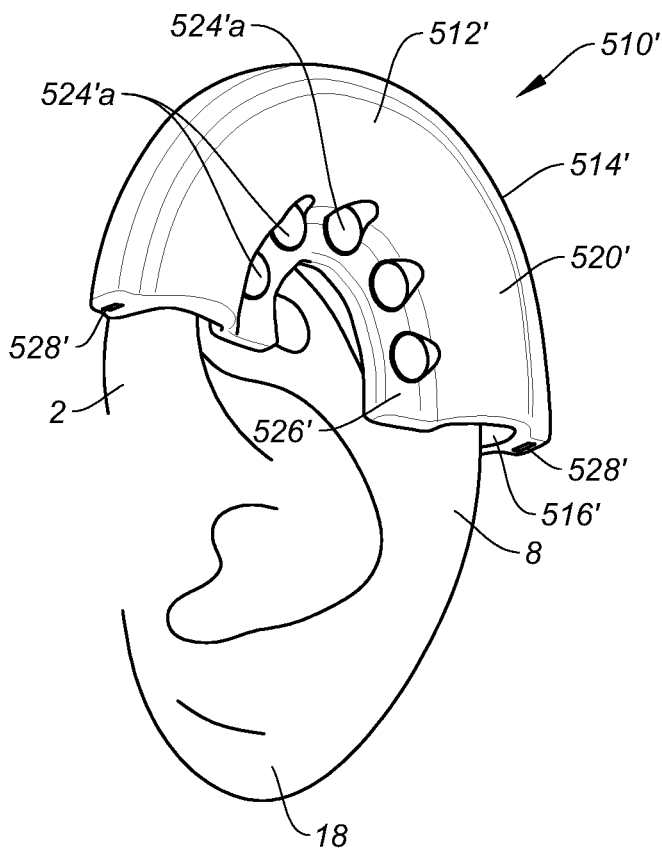
Figure 11B:
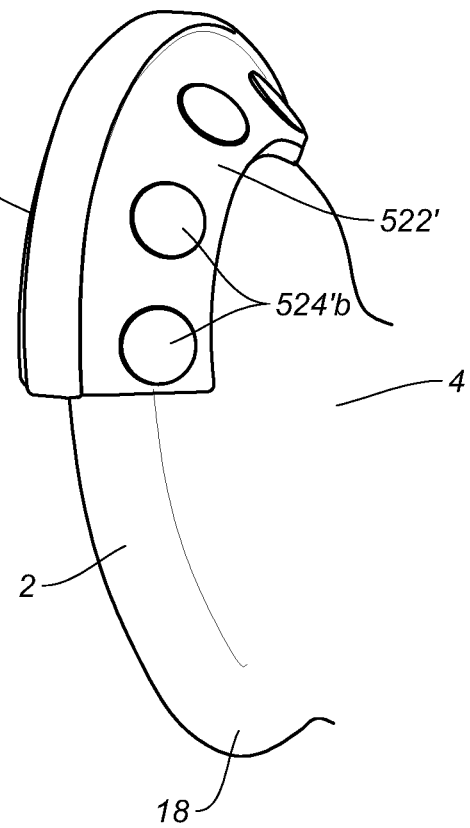
FIG. 11B shows a rear perspective view of the first corrective component and left human ear of FIG. 11A.
Figure 12A:
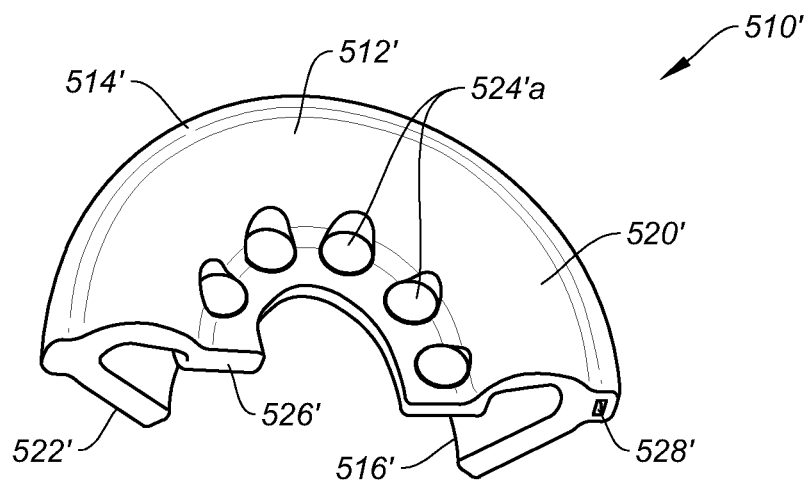
FIG. 12A shows another front perspective view of the first corrective component of FIG. 11A.
Figure 12B:
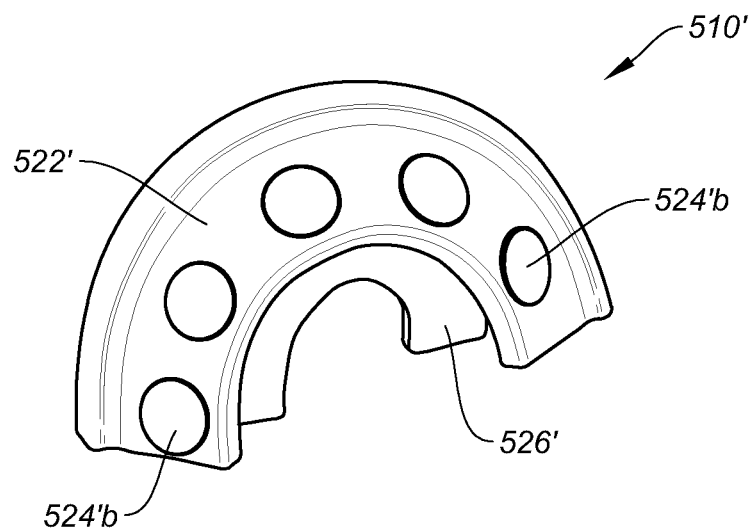

FIGS. 11A to 12B illustrate various views of another exemplary embodiment of a first corrective component 510' for use in corrective system 500. FIG. 11A shows a front perspective view of the first corrective component 510' in use with a left human ear, while FIG. 11B shows a rear perspective view of the first corrective component 510' and left human ear. FIG. 12A shows another front perspective view of the first corrective component 510', and FIG. 12B shows another rear perspective view of the first corrective component 510'.

First corrective component 510' shares similar features to first corrective component 500, with similar features or structural elements designated with the same reference numeral, followed by the symbol " ' ". Accordingly, like first corrective component 510, the main body 512' of the first corrective component 510' may be configured for placement around the helical rim 8 of the ear 2. As shown in FIGS. 12A and 12B, the main body 512' can include a generally convex outer surface 514' and a generally concave inner surface 516'. Further, the main body 512' has a front facing side 520' that extends anteriorly, and a rear facing side 522' that extends posteriorly.

The main body 512' may include therein one or more metal wires or filaments 528', which may be embedded within the main body 512'. The metal wires or filaments 528' may extend around the main body 512' along its spine, as illustrated in FIGS. 12A and 12B. The metal wires 528' allow the main body 512' to be bent and shaped to a desired shape, while holding this shape after manipulation by the physician. A flange 526' extends from the interior of the main body 512', as shown in FIGS. 11A and 12A. One or more magnets 524'a may be positioned around the flange 526', as shown in detail in FIGS. 12A and 12B. The magnets 524'a may be embedded within the flange 526', or held within pockets or cutouts formed in the flange 526', similar to what was described above.

One or more magnets 524'b may be provided and positioned on the rear facing side 522'. These one or more magnets 524'b on the rear facing side 522' may be opposite in polarity to the one or more magnets 524'a of the inner flange 526', in order to create a magnetic connection between the front facing side 520' and rear facing side 522' through the ear 2.

Unlike first corrective component 510, however, first corrective component 510' has a smaller overall profile and a generally semi-circular shape. Whereas first corrective component 510 may be configured to encircle a majority of the patient's ear 2, as shown in FIG. 8A, the first corrective component 510' of FIG. 11A may be configured for placement towards, and treatment of a deformity at, the top portion of the patient's ear 2.

Although not shown, it is understood that first corrective component 510' may be used in combination with second corrective component 540 of the corrective system 500.

Figure 13A:
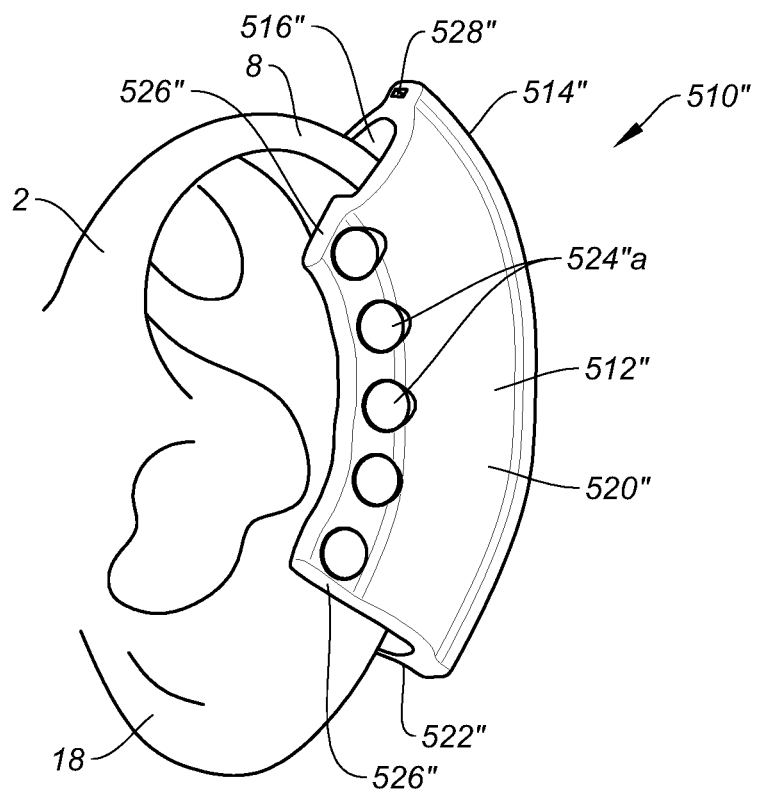
Figure 13B:
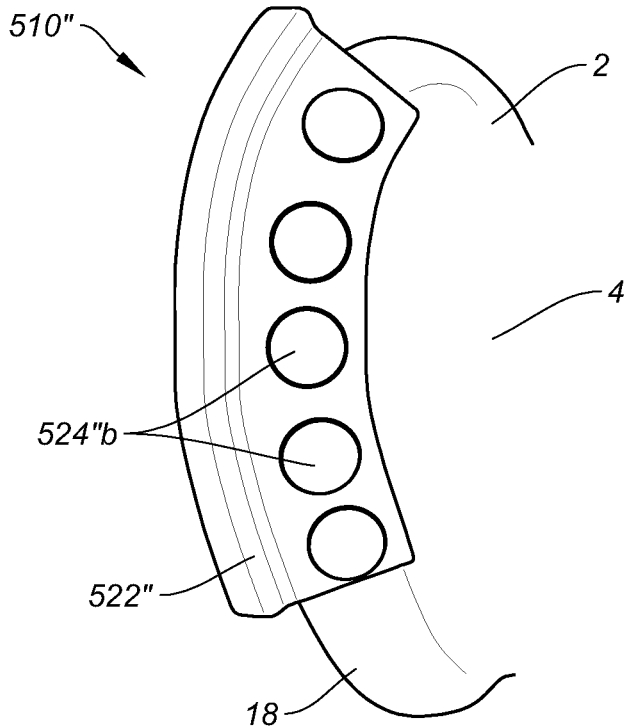
FIG. 13B shows a rear perspective view of the first corrective component and left human ear of FIG. 13A.
Figure 14A:
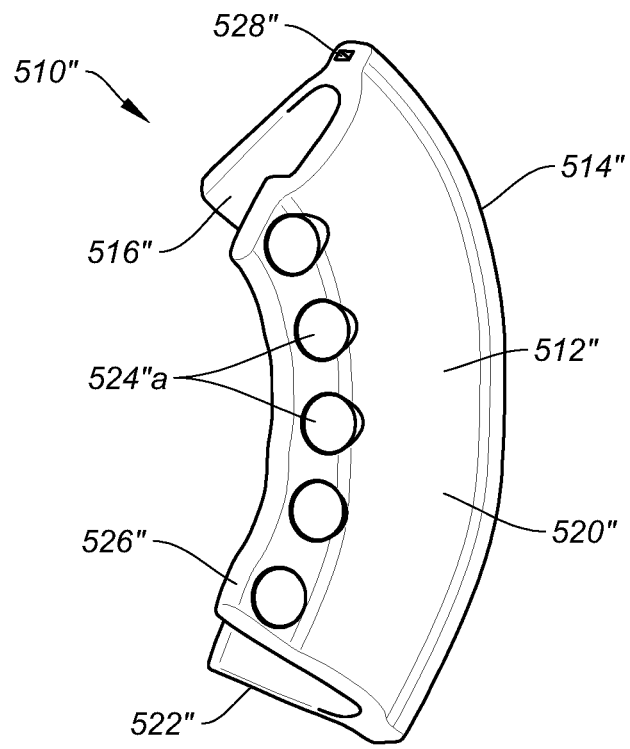
FIG. 14A shows another front perspective view of the first corrective component of FIG. 13A.
Figure 14B:
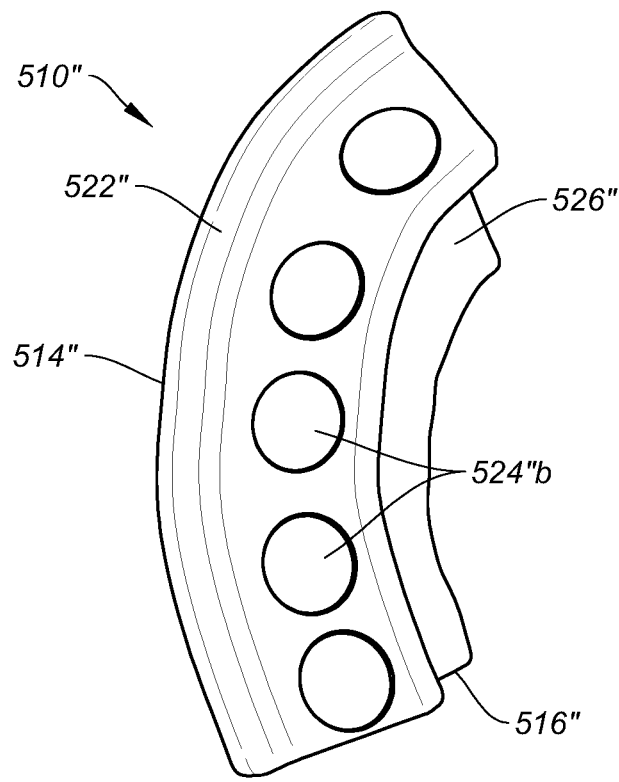
Figures 15A, 15B:
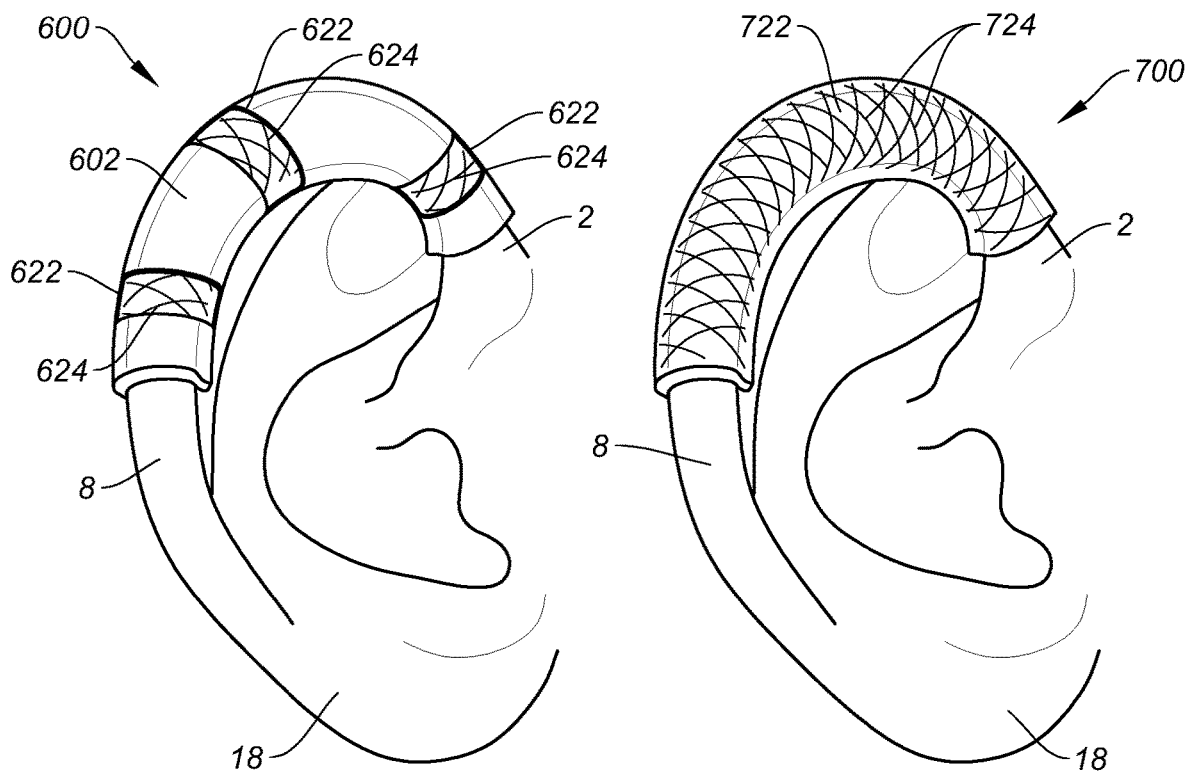
FIG. 15A illustrates a front perspective view of even still another exemplary embodiment of a corrective apparatus of the present disclosure.
FIG. 15B illustrates a front perspective view of yet even still another exemplary embodiment of a corrective apparatus of the present disclosure.

FIGS. 13A to 14B illustrate various views of yet another exemplary embodiment of a first corrective component 510" for use in corrective system 500. FIG. 13A shows a front perspective view of the first corrective component 510" in use with a left human ear, while FIG. 13B shows a rear perspective view of the first corrective component 510". FIG. 14A shows another front perspective view of the first corrective component 510", and FIG. 14B shows another rear perspective view of the first corrective component 510".

First corrective component 510" shares similar features to first corrective component 500, with similar features or structural elements designated with the same reference numeral, followed by the symbol " " ". Accordingly, like first corrective component 510, the main body 512" of the first corrective component 510" may be configured for placement around the helical rim 8 of the ear 2. As shown in FIGS. 14A and 14B, the main body 512" can include a generally convex outer surface 514" and a generally concave inner surface 516". Further, the main body 512" has a front facing side 520" that extends anteriorly, and a rear facing side 522" that extends posteriorly.

The main body 512" may include therein one or more metal wires or filaments 528", which may be embedded within the main body 512". The metal wires or filaments 528" may extend around the main body 512" along its spine, as illustrated in FIGS. 13A and 14A. The metal wires 528" allow the main body 512" to be bent and shaped to a desired shape, while holding this shape after manipulation by the physician. A flange 526" extends from the interior of the main body 512", as shown in FIGS. 13A and 14A. One or more magnets 524"a may be positioned around the flange 526", as shown in detail in FIGS. 14A and 14B. The magnets 524"a may be embedded within the flange 526", or held within pockets or cutouts formed in the flange 526", similar to what was described above.

One or more magnets 524"b may be provided and positioned on the rear facing side 522". These one or more magnets 524"b on the rear facing side 522" may be opposite in polarity to the one or more magnets 524"a of the inner flange 526", in order to create a magnetic connection between the front facing side 520" and rear facing side 522" through the ear 2.

Unlike first corrective component 510, however, first corrective component 510" has a smaller overall profile and a generally elongate shape. Whereas first corrective component 510 may be configured to encircle a majority of the patient's ear 2, as shown in FIG. 8A, the first corrective component 510" of FIG. 13A may be configured for placement along, and treatment of a deformity at, the descending helix 6b of the patient's ear 2.

Although not shown, it is understood that first corrective component 510" may be used in combination with second corrective component 540 of the corrective system 500.

While some of the corrective apparatuses of the present disclosure have been described thus far with embedded metal wires or filaments, FIG. 15A illustrates an exemplary embodiment of a corrective apparatus 600 in which the metal wires or filaments 624 are part of a metal mesh 622 or a metal weave 622. The metal mesh or weave 622 may be positioned at discrete locations on the main body 602 of the corrective apparatus 600, or the metal mesh or weave may extend throughout the main body, such as in the embodiment of a corrective apparatus 700 shown in FIG. 15B. Here, the metal wires or filaments 724 form a metal mesh or weave 722 that extends throughout the main body 702 of the corrective apparatus.

Figure 16:
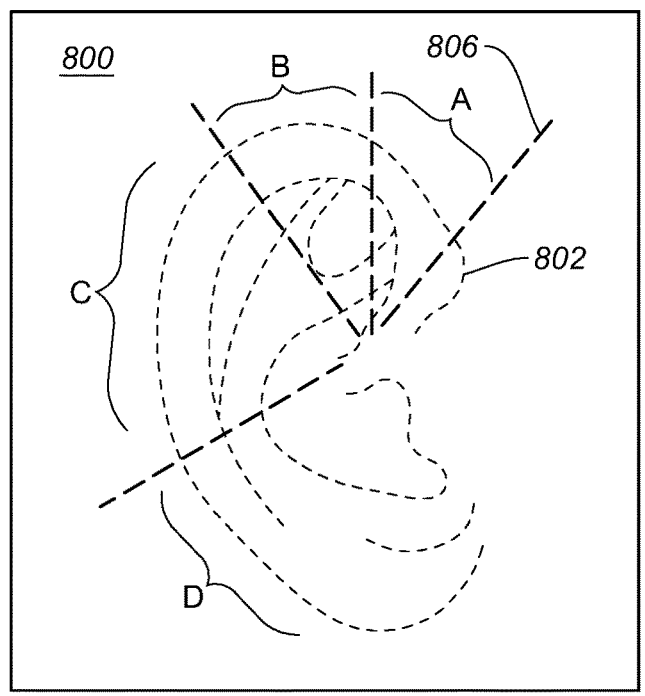
FIG. 16 illustrates an exemplary embodiment of a user's guide of the present disclosure.

Kits for correcting ear deformities in newborns and young infants can be provided which would include a set of corrective apparatuses similar to the ones shown and described herein, along with a user's guide 800 such as the one shown in FIG. 16. In this embodiment of a user's guide 800, the guide 800 may take the form of a transparent template that may include an outline of a model human ear 802. The guide 800 may be placed onto a photograph of a patient's ear. Using the line guides 806 separating the various sections (A, B, C, and D) of the ear to be treated, the physician can identify which section(s) includes the deformity or deformities. The physician can then match the section(s) with the corresponding corrective apparatus(es) for that section(s). As a visual aid, these sections (A, B, C, and D) may also be colored for ease of use.

In an exemplary method of using the corrective apparatuses of the present disclosure, a physician could first select the appropriately sized and shaped corrective apparatus using the user's guide 800 as described above, or by self-selecting the corrective apparatus from the set of apparatuses. Next, the physician can manipulate and bend the corrective apparatus to conform the shape of the corrective apparatus to a desired model ear shape. The conformed corrective apparatus can then be placed on the patient's ear for a time period to urge the patient's ear towards the desired model ear shape.

Although the corrective apparatuses and corrective systems of the present disclosure are described herein for use in newborns and young infants, it is understood that the corrective apparatuses and corrective systems may be equally applicable for use in older children as well as in adults who have external ear deformities.

Corrective apparatuses and corrective systems of the present disclosure may be customized to a patient using 3D printing techniques. For example, the dimension(s) of the model external ear may match the dimension(s) of the deformed external ear (such as in length, width, size, and/or density, among others). The components of the corrective apparatus (such as the main body) may also be printed with a three dimensional printer. The three dimensional printer may use the model external ear as the blueprint for the corrective apparatus. The three dimensional printer may match a shape and dimension(s) of the model external ear (e.g., such as a size) while printing the corrective apparatus.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A corrective apparatus for reshaping an external ear, comprising:
a standalone curved, elongated main body having a front facing side extending anteriorly and a rear facing side extending posteriorly for placement over a helical rim, the main body having an outer surface and an inner surface defining sidewalls for forming a reshaping track for the helical rim, the main body further being conformable to a desired shape and being able to maintain the desired shape during a time period of use sufficient to reshape the helical rim;
wherein the front facing side and rear facing side of the main body include magnets positioned along a bottom edge in opposing magnetic orientation to cause a magnetic attraction between the front facing side and rear facing side sufficient to hold the standalone curved, elongated main body around the helical rim.

2. The corrective apparatus of claim 1, wherein the main body further includes an elongated rear platform for placement behind the external ear.

3. The corrective apparatus of claim 2, wherein the elongated rear platform includes at least one magnet.

4. The corrective apparatus of claim 3, further including an ear component for placement against the main body to create or reshape an antihelix and having at least one magnet.

5. The corrective apparatus of claim 3, further including an ear component for insertion into a concha bowl of the ear and having at least one magnet.

6. The corrective apparatus of claim 1, wherein the main body includes a metal wire.

7. The corrective apparatus of claim 6, wherein the metal wire is embedded within the main body.

8. The corrective apparatus of claim 7, wherein the metal wire is part of a metal mesh.

9. The corrective apparatus of claim 1, wherein the outer surface of the main body has a generally convex shape.

10. The corrective apparatus of claim 1, wherein the inner surface of the main body has a generally concave shape.

11. The corrective apparatus of claim 1, wherein the main body comprises a silicone, polymer, plastic or a blend thereof.

12. The corrective apparatus of claim 1, wherein the main body comprises a metal or metal alloy.

13. The corrective apparatus of claim 1, wherein the external ear is an external ear of a newborn or young infant.

* * * * *